United States Patent [19]

Hobbs et al.

[11] Patent Number: 4,945,175

[45] Date of Patent: Jul. 31, 1990

[54] DEHYDROCYCLODIMERIZATION PROCESS START-UP PROCEDURE

[75] Inventors: Simon H. Hobbs, Chicago; Christopher D. Gosling, Roselle, both of Ill.

[73] Assignee: UOP, Des Plaines, Ill.

[21] Appl. No.: 357,221

[22] Filed: May 26, 1989

[51] Int. Cl.$^5$ ............................. C07C 2/02; C07C 2/00
[52] U.S. Cl. ..................................... 585/417; 585/415
[58] Field of Search ................................. 585/415, 417

[56] References Cited

U.S. PATENT DOCUMENTS

| | | | |
|---|---|---|---|
| 3,449,237 | 6/1969 | Jacobson et al. | 208/138 |
| 3,650,944 | 3/1972 | McCoy et al. | 208/65 |
| 4,615,792 | 10/1986 | Greenwood | 585/415 |
| 4,636,483 | 1/1987 | Kiell et al. | 502/61 |

*Primary Examiner*—Chung K. Pak
*Attorney, Agent, or Firm*—Thomas K. McBride; John F. Spears, Jr.

[57] ABSTRACT

A dehydrocyclodimerization process employing a catalyst comprising a crystalline aluminosilicate and a metal oxide component is started-up by contacting the catalyst with a start-up gas that contains less than 50 mole percent hydrogen. The catalyst is exposed to the gaseous atmosphere containing less than 50 mole percent hydrogen until a $C_2$–$C_5$ aliphatic hydrocarbon feedstock is contacted with the catalyst at dehydrocyclodimerization reaction conditions at which point hydrogen is generated as a dehydrocyclodimerization reaction product and displaces the non-hydrogen start-up gas from the process.

14 Claims, No Drawings

DEHYDROCYCLODIMERIZATION PROCESS START-UP PROCEDURE

BACKGROUND OF THE INVENTION

The present invention relates to a novel process for the dehydrocyclodimerization of $C_2$ to $C_5$ aliphatic hydrocarbons. Specifically, a process for producing aromatics via the dehydrocyclodimerization reaction, which utilizes a novel start-up method is disclosed.

Dehydrocyclodimerization is a reaction where reactants comprising paraffins and olefins, containing from 2 to 5 carbon atoms per molecule, are reacted over a catalyst to produce primarily aromatics with $H_2$ and light ends as by-products. This process is quite different from the more conventional reforming or dehydrocyclization process where $C_6$ and higher carbon number reactants, primarily paraffins and naphthenes, are converted to aromatics. These aromatics contain the same or less number of carbon atoms per molecule as the reactants from which they were formed, indicating the absence of reactant dimerization reactions. In contrast, the dehydrocyclodimerization reaction results in an aromatic product that always contains more carbon atoms per molecule than the $C_2$ to $C_5$ reactants, thus indicating that the dimerization reaction is a primary step in the dehydrocyclodimerization process. Typically, the dehydrocyclodimerization reaction is carried out at temperatures in excess of 500° F. using dual functional catalysts containing acidic and dehydrogenation components. These catalysts include acidic amorphous aluminas which contain metal promoters. Recently crystalline aluminosilicates have been successfully employed as catalyst components for the dehydrocyclodimerization reaction.

An important aspect of any catalytic process is the activity and stability of a catalyst composition when exposed to normal process conditions. The optimization of hydrocarbon process catalyst activity and stability are continuing goals of process and catalyst development efforts.

It has now been found that a dehydrocyclodimerization process utilizing a catalyst comprising a Group IIB-IVB metal component and a crystalline aluminosilicate zeolite exhibits improved initial conversion and aromatic selectivity in a dehydrocyclodimerization reaction if the process is started-up in the relative absence of hydrogen gas.

OBJECTS AND EMBODIMENTS

A principal object of this invention is to provide an improved process for the dehydrocyclodimerization of aliphatic hydrocarbons. The dehydrocyclodimerization process of this invention results in an improvement in the amount and rate that an aromatic product is produced by the dehydrocyclodimerization process. Accordingly, a broad embodiment of the present invention is directed towards a process for the dehydrocyclodimerization of dehydrocyclodimerizable hydrocarbons in the presence of a catalyst comprising a crystalline aluminosilicate zeolite, and a Group IIB-IVB metal component. The process is characterized in that the catalyst is exposed to a start-up gas containing 50 mole percent or less hydrogen during the start-up of the process and remains exposed to 50 mole percent or less hydrogen until the dehydrocyclodimerizable hydrocarbons are contacted with the catalysts at dehydrocyclodimerization reaction conditions, at which point hydrogen is produced as a reaction product and displaces any non-hydrogen start-up gas.

In a narrower embodiment, the instant dehydrocyclodimerization process is one in which $C_2-C_5$ hydrocarbons are subject to dehydrocyclodimerization in the presence of a catalyst comprising a phosphorous containing alumina, a gallium component, and a crystalline aluminosilicate zeolite having a silica to alumina ratio of at least 12. The process is characterized in that the start-up of the process comprises the steps of: (a) pressuring up the process with a dry start-up gas containing less than 30 mole percent hydrogen; (b) circulating the dry start-up gas in a closed loop through the process; (c) heating the catalyst to a temperature of about 340° C. by heating the circulating dry start-up gas; (d) contacting the $C_2-C_5$ hydrocarbon feed with the heated catalyst; (e) raising the catalyst temperature, at a rate of about 15°-30° C. per hour to about 450° C. to initiate the dehydrocyclodimerization reaction; (f) bleeding inert gas contained in the dry start-up gas from the process; (g) collecting the reaction products of the dehydrocyclodimerization process.

These as well as other embodiments of the present invention will become evident from the following more detailed description.

INFORMATION DISCLOSURE

Hydrocarbon process start-up procedures are often critical in establishing the initial performance of a catalyst in a hydrocarbon conversion process. Proper start-up procedures can insure that the hydrocarbon catalyst being utilized will be in optimum condition for hydrocarbon conversion. The ramifications of following improper start-up procedures can be low initial catalyst activity due to catalyst coke deactivation, catalyst poisoning, or complete catalyst destruction. The prior art however contains relatively few references describing detailed start-up procedures for hydrocarbon conversion processes.

U.S. Pat. No. 3,449,237 discloses a method for the start-up of a reforming process. The reforming process disclosed utilizes a specific catalyst having a platinum and uranium component. The start-up procedure consists of pressuring a reaction zone containing the above mentioned catalyst with a inert gas to about 20 psig and heating the catalyst to about 650° F. before contacting the catalyst with a sulfur free naphtha. In a similar disclosure U.S. Pat. No. 3,650,944 describes a process for reforming a sulfur free naphtha with a catalyst comprising platinum and rhenium on a porous solid carrier. The process consists of at least three reactors in a series. The start-up of the process comprises passing an inert gas through the catalyst, heating the catalyst to dehydrogenation reaction conditions and passing the substantially sulfur free naphtha into contact with the catalyst. Both of the disclosures mentioned above describe a start-up method for a reforming process. Additionally, both disclosures describe a start-up method that is useful in a reforming process where the reforming catalyst comprises platinum and rhenium or uranium. The process of this invention, however, describes a dehydrocyclodimerization process. The process occurs in the presence of a catalyst comprising a crystalline aluminosilicate zeolite and a Group IIB-IVB metal component. The instant start-up method may occur in the presence of an inert gas, or it may occur in the presence of fuel gas, light hydrocarbons, carbon monoxide, carbon dioxide, or other similar gaseous components. The essential factor of the start-up method of this invention is that the catalyst be exposed to a start-up gas comprising 50 mole percent or less hydrogen before the catalyst is brought to dehydrocyclodimerization reaction conditions.

A catalyst that is very useful in the present invention is disclosed in U.S. Pat. No. 4,636,483. The particular catalyst comprises a phosphorous containing alumina, a gallium component, and a crystalline aluminosilicate zeolite having a silica to alumina ratio of at least 12.

DETAILED DESCRIPTION OF THE INVENTION

This invention is concerned with a process for the dehydrocyclodimerization of hydrocarbons utilizing a catalytic composition comprising a Group IIB-IVB metal component and a crystalline aluminosilicate zeolite component. The process is characterized by its novel start-up method. The start-up method which surprisingly has been found to be most useful in a dehydrocyclodimerization process utilizing the above described catalyst, comprises the steps of contacting the above catalyst with a start-up gas comprising 50 mole percent or less hydrogen, quickly raising the catalyst temperature to dehydrocyclodimerization reaction conditions, and maintaining contact between catalyst and said start-up gas until the appropriate hydrocarbon feed is introduced into the dehydrocyclodimerization process. Such a start-up method has been found to optimize the catalyst stability and activity so as to produce a high amount of aromatic product components upon start-up of the process.

Processes for the conversion of light aliphatic hydrocarbons to aromatic or nonaromatic $C_6+$ hydrocarbons have been the subject of significant development efforts. The basic utility of the process is the conversion of the low cost and highly available $C_2$-$C_5$ hydrocarbons into more valuable aromatic hydrocarbons and hydrogen, or to convert the feed hydrocarbons to higher molecular weight aliphatic products. Alternatively, this may be desired simply to upgrade the value of the hydrocarbons. It may also be desired to correct an overabundance of $C_2$-$C_5$ hydrocarbons or to fulfill a need for the aromatic hydrocarbons. The aromatic hydrocarbons are highly useful in the production of a wide range of petrochemicals, with benzene being one of the most widely used basic feed hydrocarbon chemicals. The product aromatic hydrocarbons are also useful as blending components in high octane number motor fuels.

The feed stream to the dehydrocyclodimerization process is defined herein as all streams introduced into the dehydrocyclodimerization reaction zone. Included in the feed stream is the $C_2$-$C_5$ aliphatic hydrocarbon. By $C_2$-$C_5$ aliphatic hydrocarbons is meant one or more open, straight or branched chain isomers having from about two to five carbon atoms per molecule. Furthermore, the hydrocarbons in the feedstock may be saturated or unsaturated. Preferably, the $C_3$ and/or $C_4$ hydrocarbons are selected from isobutane, normal butane, isobutene, normal butene, propane and propylene. Diluents may also be included in the feed stream. Examples of such diluents include hydrogen, nitrogen, helium, argon, and neon.

The dehydrocyclodimerization process of the invention must utilize a catalyst comprising at least a metal oxide component and an aluminosilicate zeolite component. It is believed that the start-up method, critical to the process of this invention, is effective in maintaining high catalyst initial activity and aromatic selectivity, because it reduces the amount of water that may be produced at start-up. Water would, if present, be in the form of steam which is known to deactivate zeolite catalysts.

It is believed that one possible method by which water is formed during dehydrocyclodimerization process start-up is by the reaction of hydrogen with the oxide form of a metal component. As mentioned above, the water will be in the form of steam at elevated temperatures during start-up. The steam then may attack the crystalline aluminosilicate zeolite structure, eventually resulting in a loss of catalyst aromatic selectivity and catalyst conversion capability. Alternately, the change in oxidation state of the metal component, may also contribute to the loss of catalyst aromatic selectivity and catalyst conversion capability.

Obviously the mechanism mentioned above requires the presence of hydrogen, and a catalyst comprising a metal oxide component, and a crystalline aluminosilicate zeolite component. Thus, it is the objective of this process to minimize the dehydrocyclodimerization catalysts' time and temperature weighted exposure to hydrogen during the start-up of a dehydrocyclodimerization process.

The catalyst useful in the present process may be any catalyst known which comprises a metal oxide and a crystalline aluminosilicate zeolite. The metal oxide component may be any metal component that is in an oxidation state greater than zero. It is preferred that the metal oxide is a Group IIB-IVB metal oxide. Group IIB-IVB metals that are anticipated as being useful in the catalyst of this invention include zinc, cadmium, gallium, aluminum, indium, thallium, germanium, tin, and lead. It is preferred that the Group IIB-IVB metal component be gallium.

The metal component of the metal oxide may be present in any amount which is catalytically effective in a dehydrocyclodimerization process. Good results are obtained when the metal component of the metal oxide is present in an amount ranging from about 0.1 to 5.0 percent by weight on an elemental basis of the total catalytic composite. Best results are ordinarily achieved when about 0.5 to 2.0 wt. % of the metal component on all elemental basis is contained in the catalyst.

The catalyst of this process must also comprise a crystalline aluminosilicate zeolite. In particular, a group of crystalline aluminosilicate zeolites are preferred, specifically those with silica to alumina ratios of at least 12. A particularly preferred group is the one identified as the ZSM variety. Included among this ZSM variety are ZSM-5, ZSM-8, ZSM-11, ZSM-12, ZSM-35, and other similarly behaving zeolites. It is most preferred that ZSM-5 be utilized as the crystalline aluminosilicate component of the present invention. These ZSM type zeolites are generally prepared by crystallizing a mixture containing a source of alumina, a source of silica, a source of alkali metal, water, and a tetraalkylammonium compound or its precursors. Of course, other crystalline aluminosilicates which meet the silica to alumina ratio criteria may be used, such as, faujasites, L-type, mordenites, omega-type, and the like. The relative proportions of the crystalline aluminosilicate zeolite and the other components of the catalytic composite vary widely, with the zeolite content ranging from about 15 percent to about 80 percent by weight and more preferably in the range from about 50 to 70 percent by weight of composite.

The catalyst of this process may also comprise other components known to impart a dehydrocyclodimerization catalyst with desirable catalytic properties. One example of such a component is a phosphorous-containing alumina component. It is preferred that the catalyst useful in this invention comprises a phosphorous-containing alumina component.

A phosphorous-containing alumina component may be prepared by a method which comprises admixing the alumina hydrosol with a phosphorus-containing compound, the phosphorus to alumina molar ratio in the resulting phosphorus-containing admixture being from 1:1 to 1:100 on an elemental basis and subsequently mixing in a crystalline aluminosilicate and then gelling said admixture to obtain said phosphorus-containing alumina. The amount of phosphorus in the preferred catalyst can vary over a wide range. A phosphorous to aluminum molar ratio ranging from about 1:1 to about 1:100 is preferred. The 1:1 molar ratio corresponds to a phosphorus-containing alumina containing 24.7 wt. % aluminum and 20.5 wt. % phosphorus, while the 1:100 corresponds to 0.6 wt. % phosphorus and 52.0 wt. % aluminum.

The preferred catalyst of this process comprises the crystalline aluminosilicate, ZSM-5, which is present in an amount ranging from 40 to 80 wt. %. In addition, the most preferred catalyst comprises from 0.1 to 5.0 wt. % gallium and from 20 to 60 wt. % of a phosphorus-containing alumina component. Such a catalyst is described in U.S. Pat. No. 4,636,483 which is incorporated herein by reference.

The configuration of the dehydrocyclodimerization process of this invention is not a basic element or limiting characteristics of the invention. Nevertheless, in order to provide a background to the subject process, it is felt useful to describe the preferred reactor system for use in the invention. This system comprises a moving bed radial flow multi-stage reactor such as is described in U.S. Pat. Nos. 3,652,231; 3,692,496; 3,706,536; 3,785,963; 3,825,116; 3,839,196; 3,839,197; 3,854,887; 3,856,662; 3,918,930; 3,981,824; 4,094,814; 4,110,081; and 4,403,090. These patents also describe catalyst regeneration systems and various aspects of moving catalyst bed operations and equipment. This reactor system has been widely employed commercially for the reforming of naphtha fractions. Its use has also been disclosed as being useful for the dehydrogenation of light paraffins.

The preferred moving bed reactor system employs a spherical catalyst having a diameter between about 1/64-inch (0.04 cm) and ⅛-inch (0.32 cm). The catalysts useful in this process are described above.

The dehydrocyclodimerization conditions which will be employed for use with the process of the present invention will, of course, vary depending on such factors as feedstock composition and desired conversion. A desired range of conditions for the dehydrocyclodimerization of a feedstock comprising essentially $C_2$–$C_5$ hydrocarbons include a temperature from about 350° to about 700° C., a pressure from about 0.25 to about 20 atmospheres, and a liquid hourly space velocity from about 0.5 to about 20 $hr^{-1}$. The preferred process conditions are a temperature in the range from about 400° to 650° C., a pressure in the range of from 0.25 to 10 atmospheres, and a liquid hourly space velocity of between 0.5 and 10.0 $hr^{-1}$. It is understood that, as the average carbon number of the feed increases, a temperature in the lower end of temperature range is required for optimum performance and, conversely, as the average carbon number of the feed decreases, a higher temperature is required in the reaction zone.

According to the present invention, the dehydrocyclodimerization reaction zone hydrocarbon feed stream is contacted with a catalytic composite in a dehydrocyclodimerization reaction zone maintained at dehydrocyclodimerization conditions. This contacting may be accomplished by using the catalytic composite in a fixed bed system, a moving bed system, a fluidized bed system, or in a batch-type operation; however, in view of the danger of attrition losses of the valuable catalyst and of the well-known operation advantages, it is preferred to use either a fixed bed system or a dense-phase moving bed system such as shown in U.S. Pat. No. 3,725,249. It is contemplated that the contacting step can be performed in the presence of a physical mixture of particles of any dehydrocyclodimerization or similarly behaving catalyst of the prior art.

In a fixed bed system or a dense phase moving bed, the feed stream is preheated by any suitable heating means to the desired reaction temperature and then passed into a dehydrocyclodimerization zone containing a bed of desired catalytic composite. It is, of course, understood that the dehydrocyclodimerization zone may be one or more separate reactors with suitable means therebetween to assure that the desired conversion temperature is maintained at the entrance to each reactor. It is also important to note that the reactants may be contacted with the catalyst bed in either upward, downward, or radial flow fashion, with the latter being preferred. In addition, the reactants may be in the liquid phase, admixed liquid-vapor phase, or a vapor phase when they contact the catalyst, with the best results obtained in the vapor phase. The dehydrocyclodimerization system then preferably comprises a dehydrocyclodimerization zone containing one or more fixed or dense phase moving beds of a catalytic composite described above. In a multiple bed system, it is, of course, within the scope of the present invention to use one dehydrocyclodimerization catalyst composite in less than all of the beds with another dehydrocyclodimerization or similarly behaving catalyst being used in the remainder of the beds. In a multiple reactor dehydrocyclodimerization zone, there may be one or more separate reactors with suitable heating means therebetween to compensate for any heat loss encountered in each catalyst bed. Specific to the dense phase moving bed system, it is common practice to remove catalyst from the bottom of the reaction zone, regenerate it by conventional means known to the art, and then return it to the top of the reaction zone.

The instant process is characterized in that it utilizes a unique start-up method that has been tailored to be effective when used in conjunction with a metal oxide/crystalline aluminosilicate zeolite dehydrocyclodimerization catalyst. The start-up method is able to maximize the initial aromatic conversion and selectivity of the above described catalyst in a dehydrocyclodimerization process.

It should be noted that by start-up we mean that this method can be used in any instance where a dehydrocyclodimerization catalyst that is not being contacted with a hydrocarbon feedstock is prepared for contact with a hydrocarbon feedstock. This can occur when the catalyst is fresh and newly loaded into the process. It can occur during a process upset when the hydrocarbon feed has been temporarily removed from the unit. It can also occur after the catalyst has been regenerated in the absence of a hydrocarbon feedstock. Such catalyst regeneration may occur in a batch or continuous catalyst regeneration system.

The method for starting-up the dehydrocyclodimerization process of this invention comprises exposing the catalyst of this invention to a start-up gas containing 50 mole percent or less hydrogen under strictly limited conditions of time and temperature. The catalyst is contacted with this start-up gas during all aspects of process start-up including process pressurization, start-up gas circulation, catalyst heat-up, and continuing up until the point that the hydrocarbon feed is introduced into the process and the dehydrocyclodimerization reaction occurs. The catalyst heat up should be accomplished as rapidly as the mechanical limitations of the catalyst and equipment will allow. It is preferred that the start-up gas contains 30 mole percent or less hydrogen and it is most preferred that the start-up gas contain essentially no hydrogen. By essentially no hydrogen, it is meant 2.0 mole % or less hydrogen in the start-up gas.

Minimizing the hydrogen in the start-up gas, minimizes the loss in catalyst activity resulting from zeolite deactivation. The process described in this invention is cognizant of the fact that it may be impossible for a refiner to completely eliminate hydrogen from the process start-up gas. For this reason, the maximum level of hydrogen in the start-up gas that is likely to be tolerated by the catalyst during start-up is about 50 mole percent.

The start-up gas obviously must contain other gaseous components besides hydrogen. Any gaseous component used in the start-up gas must be capable of remaining gaseous at process start-up conditions. Such start-up conditions include temperatures of from −40° to 450° C. and pressures of from 0.25 to 20 atmospheres. Gaseous components which fall into this definition include the noble gases, including helium, neon, and argon. Gaseous hydrocarbons may also be used in the start-up gas. Such gaseous hydrocarbons include, but are not limited to, methane, ethane, propane, fuel gas, and the like hydrocarbons. Additionally, the following gaseous components may be useful in the start-up gas; nitrogen. Obviously, mixtures of any and all of the above named gaseous components may be utilized as the start-up gas. It is, however, preferred that the start-up gas comprise nitrogen or fuel gas or mixtures thereof.

The specific start-up procedure is not critical to the invention. It is critical, however, that the start-up gas employed in the start-up procedure contains 50 mole percent or less hydrogen, and that the time the catalyst is exposed to high temperature start-up gas be limited.

The start-up method detailed below is not intended to limit the scope of the process of this invention. It is merely intended to present one of many possible methods of starting-up a dehydrocyclodimerization process such as that disclosed in this invention.

The start-up of the process of this invention will be preceeded by prestart-up activities. Such prestart-up activities may include equipment leak testing, reactor dry-out, reactor catalyst loading and the initial purging of the unit with the desired start-up gas. The unit purge is undertaken to eliminate any oxygen that may be contained in the unit. Once these initial start-up tasks have been completed the process is ready for operation.

To begin the start-up of the process, the reactor system of the process is pressurized with dry start-up gas. The pressure of the system may range from 0.25 to 20 atmospheres, consistent with the design or operating pressure of the unit. The start-up gas utilized may be chosen from the list of start-up gases detailed herein above. It is an important aspect that the start-up gas used in this process is dry. By dry it is meant that the start-up gas should contain less than 20 ppm water and preferably less than 5 ppm water. If the start-up gas contains large amounts of water then the effectiveness of the start-up of the process in the relative absence of hydrogen will be negated.

Once the reactor system has been pressured with the start-up gas, the gas is circulated throughout the process with the process recycle compressors. At this point, the start-up gas will be heated utilizing the hydrocarbon feed preheat furnaces. The heated gases will be passed across the dehydrocyclodimerization catalyst and the catalyst heated to a temperature of about 340° C. The time during which hot start-up gas is in contact with the catalyst should be minimized.

Once the catalyst has reached a temperature of about 340° C., the hydrocarbon feed may be introduced into the catalyst bed. At a temperature of about 340° C., there will be little, if any, dehydrocyclodimerization occurring in the reaction zone. Therefore, at this point, the catalyst bed temperature should be raised to a temperature of about 450° C., at a rate of about 15° to 30° C. per hour in order to initiate and sustain the dehydrocyclodimerization reaction. Once the dehydrocyclodimerization reaction is initiated, hydrogen will be produced as a reaction product. At this point, the pressure of the process will be controlled by bleeding the gaseous products of the reaction from the unit. Any inert gases, such as nitrogen, helium, argon, and the like, contained in the start-up gas may be bled from the process, typically from the high pressure separator at this time. Finally, once the dehydrocyclodimerization reaction is occurring, the liquid reaction products of the dehydrocyclodimerization process can be collected.

As mentioned, this start-up procedure or permeations thereof, may be utilized when the process is being initially started-up; started-up following maintenance or emergency shut-down; or started-up following catalyst replacement or the like. It is also anticipated in a process utilizing continuous catalyst regeneration, that the start-up method outlined above may be engineered into the continuous process such that the regenerated catalyst from the continuous regeneration step of a continuous regeneration process will not be exposed to any hydrogen after regeneration and until it is contacted with the hydrocarbon feedstock.

The following example serves to illustrate the process of this invention. The example should not, however, be construed as limiting the scope of the invention as set forth in the claims as there are many variations which may be made thereon without departing from the spirit of the invention as those skilled in the art will recognize.

EXAMPLE I

The following tests were performed to demonstrate the benefit of utilizing a dehydrocyclodimerization start-up procedure that does not utilize hydrogen.

A dehydrocyclodimerization catalyst was prepared as follows: A first solution was prepared by adding phosphoric acid to an aqueous solution of hexamethylenetetramine (HMT). A second solution was prepared by adding a ZSM-5 type zeolite to enough alumina sol, prepared by digesting metallic aluminum in hydrochloric acid, to yield a zeolite content in the finished catalyst equal to about 50–75 wt. %. These two solutions were commingled to achieve a homogeneous admixture of HMT, phosphorus, alumina sol, and zeolite. This admixture was dispersed as droplets into an oil bath maintained at about 200° F. The droplets remained in the oil bath until they set and formed hydrogel spheres. These spheres were removed from the oil bath, water washed, air dried, and calcined at a temperature of about 900° F. A solution of gallium nitrate was utilized to impregnate the spheres to achieve a gallium content on the finished catalyst equal to about 1 wt. %. After impregnation the spheres were calcined a second time, in the presence of steam, at a temperature of about 1200° F.

Further information of the catalyst preparation method can be obtained from U.S. Pat. No. 4,636,483.

Two quantities of the catalyst above were subjected to a pilot plant start-up procedure, utilizing hydrogen as the start-up gas in the first test, and nitrogen as the start-up gas in the second test.

The start-up method consisted of purging the pilot plant with the start-up gas followed by heating of the reaction zone to 550° C. for leak testing of the pilot plant in the presence of the same start-up gas. After leak testing, propane was introduced into the pilot plant reactor at dehydrocyclodimerization reaction conditions. The dehydrocyclodimerization reaction conditions included a temperature of 540° C., a pressure of 1.0 atmosphere gauge and a liquid hourly space velocity of 0.8 hr$^{-1}$. The products of the reaction of each test were analyzed and the $C_3$–$C_4$ conversion and aromatic selectivity values for each test were determined after the catalyst of each test had been exposed to the propane feed for 34 hours. The above results are detailed in Table I below.

TABLE 1

| Test # | 1 | 2 |
|---|---|---|
| Start-up Gas | $H_2$ | $N_2$ |
| $C_3$–$C_4$ Conversion, Wt % | 62.2 | 68.3 |
| Aromatic Selectivity, Wt % | 56.1 | 58.8 |

The results in Table I above clearly indicate that a dehydrocyclodimerization process that utilizes a gas besides hydrogen as a start-up gas exhibits a dehydrocyclodimerization performance superior to that of a process utilizing a hydrogen start-up gas.

EXAMPLE II

A dehydrocyclodimerization catalyst as prepared in Example I was subjected to a soaking step for 100 hours in the presence of a start-up gas consisting of 40 mole % nitrogen and 60 mole percent methane at 580° C. The soaked catalyst was then subjected to a synthetic regeneration step in which the catalyst was exposed to a gas comprising 99 mole % nitrogen, 1 mole % oxygen and 600 mole ppm of water at 530° C., for 6 hours at a gas hourly space velocity of 2400 hr$^{-1}$.

The soaked and regenerated catalyst was then placed in a dehydrocyclodimerization pilot plant subjected to a nitrogen gas start-up after which the plant, subjected to a nitrogen gas start-up after which the $C_3/C_4$ conversion ability of the catalyst was evaluated utilizing the pilot plant conditions detailed in Example I. The results of the pilot plant testing are found in Table III below.

TABLE II

| Start Up Gas (Mole %) | Test Catalyst 40%$N_2$/60% $CH_4$ | Fresh Catalyst — |
|---|---|---|
| Time Hours | $C_3C_4$ Conversion Wt % | $C_3/C_4$ Conversion Wt % |
| 30 | 75.0 | 75.4 |

We claim:

1. A process for the dehydrocyclodimerization of $C_2$–$C_5$ hydrocarbons in the presence of a catalyst comprising a phosphorous containing alumina, a gallium component, and a crystalline aluminosilicate zeolite having a silica to alumina molar ratio of at least 12 characterized in that the start-up of the process comprises:
   (a) contacting the catalyst with a dry start-up gas comprising 50 mole percent or less hydrogen;
   (b) heating the catalyst in the presence of the dry start-up gas to a temperature at which the dehydrocyclodimerization reaction will occur;
   (c) passing the $C_2$–$C_5$ hydrocarbons across the heated catalyst and thereby producing a dehydrocyclodimerization reaction product including hydrogen; and
   (d) displacing the non-hydrogen dry start-up gas from the process with the gaseous product of the dehydrocyclodimerization reaction including hydrogen.

2. The process of claim 1 further characterized in that the crystalline aluminosilicate zeolite component of the catalyst is ZSM-5.

3. The process of claim 1 further characterized in that the gallium component of the catalyst is present in an amount ranging from about 0.1–5.0 percent by weight of the total catalytic composite.

4. The process of claim 1 further characterized in that the phosphorous containing alumina component of the catalyst is present in an amount ranging from 20 to 60 percent by weight of the total catalytic composite and where the phosphorous to alumina ratio of the phosphorous containing alumina ranges from 1:1 to 1:100.

5. The process of claim 1 further characterized in that the catalyst and the start-up gas are maintained within the temperature range of 10° to 540° C.

6. The process of claim 1 further characterized in that the start-up gas comprises in addition to 50 mole percent or less of hydrogen, a gas or mixture of gases selected from the group consisting of nitrogen, ethane, methane, propane, fuel gas, helium, argon, and any other hydrocarbons that remain gaseous at dehydrocyclodimerization start-up conditions.

7. The process of claim 1 further characterized in that the start-up gas consists essentially of nitrogen and 50 mole percent or less of hydrogen.

8. The process of claim 1 further characterized in that the start-up gas comprises 30 mole percent or less of hydrogen.

9. The process of claim 1 further characterized in that the start-up gas is dry.

10. A process for the dehydrocyclodimerization of $C_2$–$C_5$ hydrocarbons in the presence of a catalyst comprising a phosphorous containing alumina, a gallium component, and a crystalline aluminosilicate zeolite having a silica to alumina molar ratio of at least 12, characterized in that the start-up of the process comprises the steps of:

(a) pressuring the process with a dry start-up gas containing less than 30 mole percent hydrogen;

(b) circulating the dry start-up gas in a closed loop through the process;

(c) heating the catalyst to a temperature of about 340° C. by heating the circulating dry start-up gas;

(d) contacting the $C_2$–$C_5$ hydrocarbon feed with the heated catalyst;

(e) raising the catalyst temperature to about 450° C. at a rate of about 15°–30° C. per hour to sustain the dehydrocyclodimerization reaction;

(f) bleeding any inert gases contained in the dry start-up gas from the process; and (g) collecting the reaction products of the dehydrocyclodimerization process.

11. The process of claim 10 further characterized in that the dry start-up gas comprises of components or mixtures of components selected from the group consisting of nitrogen, helium, argon, neon, methane, ethane, fuel gas and any other hydrocarbon that remains gaseous at process start-up conditions.

12. The process of claim 11 further characterized in that the dry start-up gas comprises essentially pure nitrogen.

13. The process of claim 11 further characterized in that the dry start-up gas comprises essentially pure fuel gas.

14. The process of claim 10 further characterized in that the dehydrocyclodimerization of the $C_2$–$C_5$ hydrocarbons occurs in a moving catalyst reactor connected to a continuous catalyst regeneration system.

* * * * *